(12) United States Patent  
Corvaglia

(10) Patent No.: US 9,709,481 B2  
(45) Date of Patent: Jul. 18, 2017

(54) METHOD FOR DETERMINING THE TACK OF A MATERIAL

(71) Applicant: ALENIA AERMACCHI S.p.A., Rome (IT)

(72) Inventor: Stefano Giuseppe Corvaglia, Lecce (IT)

(73) Assignee: ALENIA AERMACCHI S.p.A., Rome (IT)

( * ) Notice: Subject to any disclaimer, the term of this patent is extended or adjusted under 35 U.S.C. 154(b) by 0 days.

(21) Appl. No.: 14/614,062

(22) Filed: Feb. 4, 2015

(65) Prior Publication Data

US 2015/0226661 A1    Aug. 13, 2015

(30) Foreign Application Priority Data

Feb. 7, 2014   (IT) .............................. TO2014A0101

(51) Int. Cl.
*G01N 19/04* (2006.01)

(52) U.S. Cl.
CPC ..... *G01N 19/04* (2013.01); *G01N 2203/0091* (2013.01); *G01N 2203/0262* (2013.01)

(58) Field of Classification Search
CPC ..................................................... G01N 19/04
See application file for complete search history.

(56) References Cited

U.S. PATENT DOCUMENTS

| 3,303,697 A | 2/1967 | Schroeder | |
|---|---|---|---|
| 2012/0015288 A1* | 1/2012 | Ikeda | G03F 1/68 430/5 |
| 2013/0098232 A1* | 4/2013 | Locke | F41H 5/04 89/36.02 |
| 2013/0129957 A1* | 5/2013 | Zhao | C09J 7/041 428/40.1 |

FOREIGN PATENT DOCUMENTS

| FR | 1 580 947 A | 9/1969 |
|---|---|---|
| JP | S56-111439 A | 9/1981 |
| WO | WO 2012/157686 A1 | 11/2012 |

OTHER PUBLICATIONS

Italian Search Report for corresponding Italian Patent Application No. TO2014A000101 mailed Oct. 10, 2014.
Rothman, L.B., "Properties of Thin Polyimide Films", *Journal of the Electrochemical Society*, 127(10): 2216-2220 (1980).

* cited by examiner

*Primary Examiner* — Hezron E Williams
*Assistant Examiner* — David Z Huang
(74) *Attorney, Agent, or Firm* — Merchant & Gould P.C.

(57) ABSTRACT

A method determines the tack of a material placed in contact with a surface. A sample is provided of the material, the sample including a sheet whose width increases from a first narrow end to a second wide end. The sample is applied to an upwards facing supporting surface of plate. The sample is compacted against the supporting surface of plate and a weight is attached to the first end of the sample. The plate is turned over in such a way that the supporting surface faces downwards. The detachment of the sample from the supporting surface is measured in terms of distance detached from the first end of the sample as a function of time.

9 Claims, 2 Drawing Sheets

METHOD FOR DETERMINING THE TACK OF A MATERIAL

This application claims benefit of Serial No. TO2014A000101, filed 7 Feb. 2014 in Italy and which application is incorporated herein by reference. To the extent appropriate, a claim of priority is made to the above disclosed application.

BACKGROUND OF THE INVENTION

This invention relates in general to methods for determining the tack of materials, in particular composite materials of the type comprising a resin matrix reinforced with fibre material.

Methods for determining the tack of adhesives are known. In these materials the forces responsible for tack are in general various orders of magnitude larger than the composite materials in question. In addition to this, the phenomena underlying attachment of the materials are significantly different. It is therefore felt that the tests developed for adhesives are unsuitable for determining the tack of composite materials.

On the other hand, in the industrial environment there is a need to develop a method of test which can be used to evaluate and compare materials used for the forming of components or for application to a mould or mandrel for the manufacture of particular pieces.

SUMMARY OF THE INVENTION

According to this invention a method for determining the tack of a material placed in contact with a surface is therefore provided and comprises the following stages:
   providing a sample of said material, the sample comprising a sheet whose width increases from a first narrow end to a second wide end;
   applying the sample to the an upward facing supporting surface of a plate;
   compacting the sample against the surface of the supporting plate;
   attaching a weight to the first end of the sample;
   turning the plate over in such a way that the supporting surface faces downwards; and
   measuring detachment of the sample from the supporting surface from the first end of the sample in terms of distance detached as a function of time.

Although the process according to the invention has been envisaged in relation to determination of the tack of composite materials, it may also find application for other materials which exhibit tack.

BRIEF DESCRIPTION OF THE DRAWINGS

Further features and advantages of the invention will be described in greater detail in the following detailed description of an embodiment provided by way of a non-limiting example with reference to the appended drawings in which.

DETAILED DESCRIPTION OF THE PREFERRED EMBODIMENTS

Figure 1:
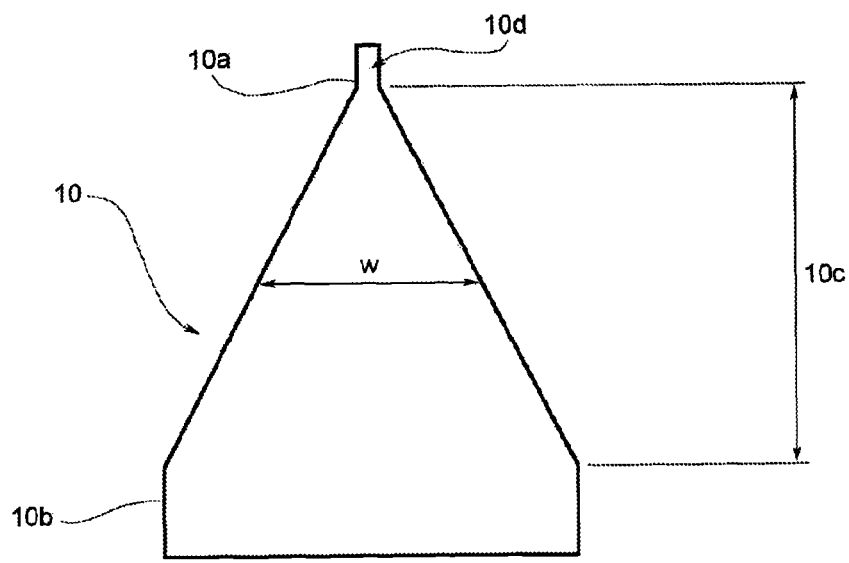
FIG. 1 is a plan view of an example of a sample used in the method according to the invention.

With reference to FIG. 1, this shows a sample 10 for use in a process for determining tack according to the invention. This sample 10 comprises a sheet having a width w which increases from a first narrow end 10a to a second wide end 10b. In particular sample 10 has a longitudinal section 10c having a width w that increases linearly towards second end 10b of the sample. Sample 10 also has a tab portion 10d at its first end 10a, the function of which will be clarified below.

Sample 10 is made of a material whose tack with regard to the surface of another material is to be tested. This tack may be the intrinsic tack of the material or the tack imparted to the material by the interposition of an adhesive agent or tackifier between the material under test and the surface (or other material where it is desired to test tack between two similar or different materials; in this case the substrate material will be anchored to the plate by two-sided adhesive tape applied over the entire surface area).

In particular, sample 10 may be made of a composite material comprising a resin matrix reinforced with fibre material.

Sample 10 may be obtained by cutting the material under test into the desired shape, for example using masks.

Figure 2:
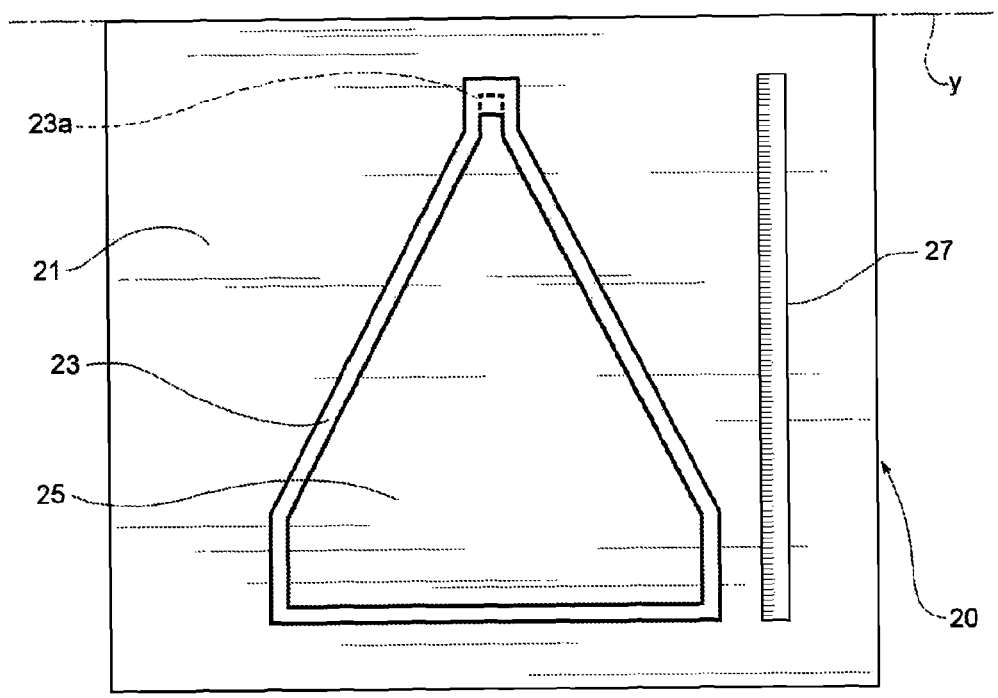
FIG. 2 is a plan view of a plate supporting the sample in FIG. 1.

With reference to FIG. 2, this shows a plate 20 for use in the method according to the invention.

Plate 20 comprises a supporting surface 21 to which it is intended that sample 10 should be applied. This plate may for example be of metal material, such as aluminium. A mask 23 of non-adhering material delimiting an area of application 25 suitable for receiving sample 10 is preferably located on supporting surface 21 of plate 20. As will be seen, the shape of application area 25 approximately matches the shape of sample 10. In addition to this, a graduated scale 27 for measuring length, arranged parallel to the longitudinal direction of application area 25, which when in use corresponds to the longitudinal direction of sample 10, is located on supporting surface 21 of plate 20.

Figure 3:
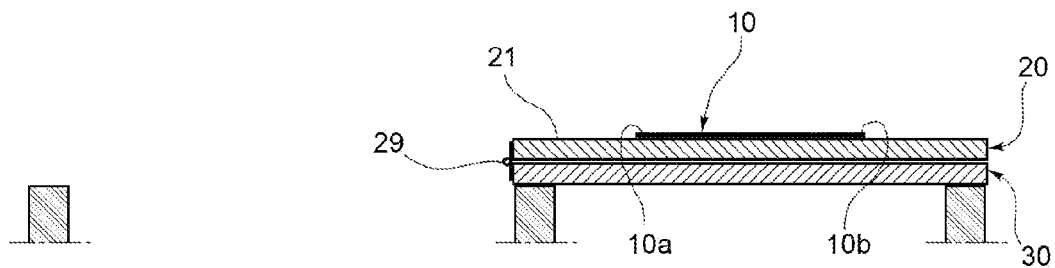
FIGS. 3 to 6 are diagrammatical views showing different operating stages in the method according to this invention.

Preferably, plate 20 is attached to a base 30 by means of a hinge 29, as may be seen in FIG. 3. Through this arrangement, plate 20 may rotate with respect to base 30 about an axis of rotation y located perpendicularly to the longitudinal direction of area 25 to which sample 10 is applied. Plate 20 can therefore rotate between a starting position (shown in FIGS. 3 and 4) in which supporting surface 21 faces upwards, and an overturned position (shown in FIGS. 5 and 6) in which supporting surface 21 faces downwards.

An embodiment of a method for determining tack according to the invention will now be described with references to FIGS. 3 to 6.

Initially, plate 20 is in the starting position on base 30. Supporting surface 21 may be first cleaned with specific solvents to remove any substances which might have an adverse effect on the measurements. Plate 20 may also be placed in a climatized chamber (not illustrated) to condition the plate to a particular temperature and relative humidity, depending upon the specific conditions which it is desired to test. Sheet 10 of the material under test, which has not yet been applied to plate 20, is also placed within the climatized chamber.

Subsequently, an adhesive agent or tackifier may or may not be applied to previously conditioned plate 20 in the area of application 25 (or another material may be placed in between if it is desired to test tack between two similar or different materials; in this case the substrate material will be anchored to the plate with two-sided adhesive tape applied over the entire surface area).

When the tackifier has been applied, plate 20 may undergo a second conditioning in the climatized chamber, again together with sample 10, for the necessary time determined by means of individual tests ("tackifier flash time").

Sample 10 will then be applied to supporting surface 21 of plate 20, as illustrated in FIG. 3, in application area 25 which may have been treated with tackifier.

Figure 4:
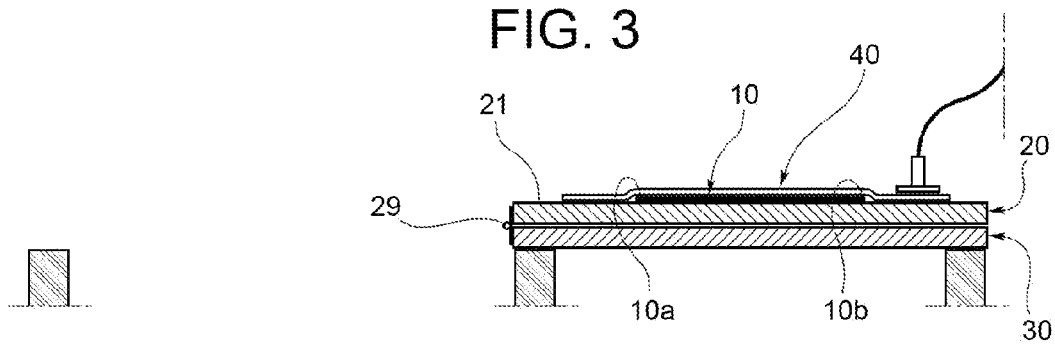

As illustrated in FIG. 4, a vacuum bag 40 is then fitted over sample 10 and sample 10 is compacted against supporting surface 21 of plate 20 under vacuum. The vacuum pressure applied and the vacuum application time will depend on the test conditions. In accordance with alternative embodiments (not illustrated) compaction may be performed by means of a roller, or manually, according to the conditions which it is desired to simulate.

Once the vacuum bag has been removed, plate 20, together with applied and compacted sample 10, is again subjected to conditioning in a climatized chamber at a controlled temperature and humidity for a desired length of time.

A weight 50 (shown in FIGS. 5 and 6) is then attached to first end 10a of the sample, more specifically to tab portion 10d. This may be done, for example, by applying a clip or spring to which weight 50 is attached to the tab portion 10d. In order to allow the clip to be attached to tab portion 10d the latter must be dimensioned to have a length which partly overlaps mask 23. This prevents the portion of tab 10d from adhering completely to supporting surface 21 during compaction under vacuum, thus leaving a free portion which will allow the clip with weight 50 to be inserted. The area of overlap between mask 23 and tab portion 10d is shown by a dashed line in FIG. 2 and is designated by reference 23a.

Figure 5:
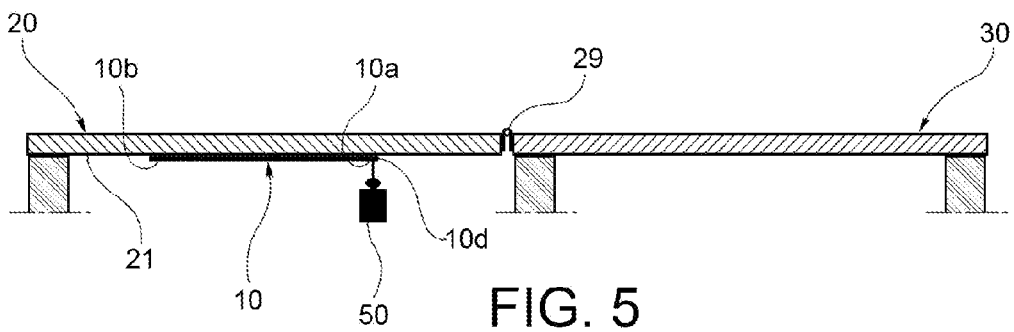

As illustrated in FIG. 5, plate 20 is then turned upside down by causing it to rotate about hinge 29.

Figure 6:
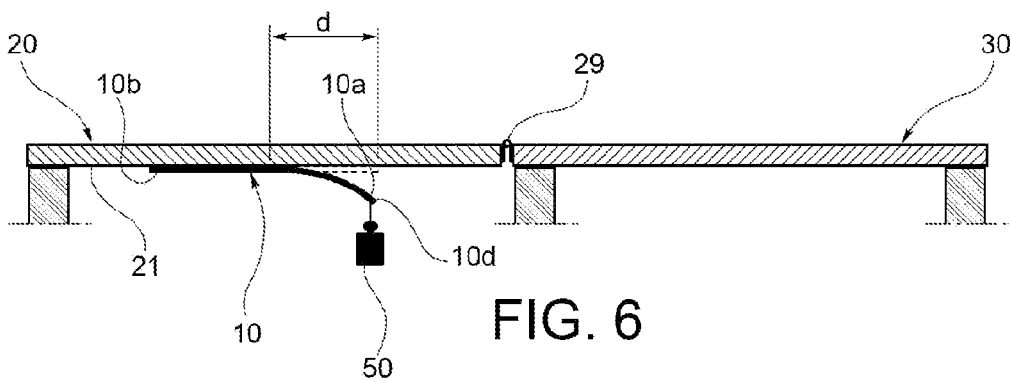

As a result of the effect of plate 50 attached to first end 10a, sheet 10 becomes progressively detached from supporting surface 21 of plate 20, starting from first end 10a (FIG. 6). Thanks to graduated scale 27 located on supporting surface 21 the distance d through which sheet 10 becomes detached at a particular time following the application of weight 50 can be measured.

By reading off detachment distance d at intervals of time defined according to the circumstances it is possible to draw a graph of the increase in detachment distance d of sheet 10 as a function of time.

By making measurements on the same material, but varying different parameters such as tackifier flash time, temperature, relative humidity, aging of the material and application time of the vacuum, it is possible to draw graphs to evaluate the correlation between these parameters and tack.

One method of assessing tack is to consider the graphs obtained for detachment distance d as a function of time, by determining the area subtended by each curve starting from a particular time after application of the weight (for example 30 seconds after application of the weight) in order to rule out any initial errors due to the different speeds at which the weight is allowed to fall, up to a maximum predetermined time (for example 10 minutes). Bearing in mind that this subtended area is proportional to the detachment of sheet 10 from plate 20, tack can be considered to be directly proportional to the reciprocal of the calculated area.

By then drawing the graph of the reciprocal of the area as a function of a variable parameter (for example temperature or another of the parameters indicated above) it is possible to observe the change in tack as a given characteristic varies.

What is claimed is:

1. A method for assessing tack of a material contacting a surface, comprising the following steps:
   providing a sample of said material, the sample comprising a sheet having a width increasing from a narrow first end of the sample to a wide second end of the sample;
   laying the sample on a support surface of a plate facing upwards;
   compacting the sample against the support surface of the plate;
   attaching a weight to the first end of the sample;
   reversing the plate to cause the support surface to face downwards; and
   measuring detachment of the sample from the support surface, comprising measuring a detachment distance from the first end of the sample at a time after detachment has begun.

2. A method according to claim 1, wherein the sample comprises a longitudinal section having a width linearly increasing from the first end toward the second end of the sample.

3. A method according to claim 1, wherein the sample comprises a tab portion at the first end which is configured for attachment of the weight.

4. A method according to claim 1, wherein a mask of adhesion-preventing material is disposed on the support surface of the plate, said mask limiting a laying area for receiving the sample.

5. A method according to claim 1, wherein a graduated scale is disposed on the support surface of the plate, said scale being adapted for measuring detachment of the sample from the support surface.

6. A method according to claim 1, wherein the plate is hinged to a base, said plate being rotatable between a start position wherein the support surface is facing upwards, and a reversed position wherein the support surface is facing downwards.

7. A method according to claim 1, wherein said material is a composite material comprising a resin matrix reinforced with fiber material.

8. A method according to claim 1, wherein before laying the sample on the support surface of the plate, the sample and the plate are subjected to conditioning at predetermined humidity and temperature.

9. A method according to claim 1, wherein after compacting, the sample and the plate are subjected to conditioning at predetermined humidity and temperature.

* * * * *